(12) United States Patent
Piccirillo et al.

(10) Patent No.: US 10,653,431 B2
(45) Date of Patent: May 19, 2020

(54) DRILL ASSEMBLIES AND METHODS FOR DRILLING INTO BONE

(71) Applicant: Medos International Sárl, Le Locle (CH)

(72) Inventors: Justin M. Piccirillo, Uxbridge, MA (US); Thomas Piscatelli, Walpole, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 796 days.

(21) Appl. No.: 15/181,506

(22) Filed: Jun. 14, 2016

(65) Prior Publication Data

US 2017/0354423 A1 Dec. 14, 2017

(51) Int. Cl.
*A61B 17/16* (2006.01)
(52) U.S. Cl.
CPC ...... *A61B 17/1631* (2013.01); *A61B 17/1615* (2013.01); *A61B 17/1633* (2013.01)
(58) Field of Classification Search
CPC .................. A61B 17/1631; A61B 17/1633
USPC .................. 606/112, 116, 127, 159, 200
See application file for complete search history.

(56) References Cited

U.S. PATENT DOCUMENTS

| | | |
|---|---|---|
| 216,858 A | 6/1879 | Justi |
| 3,071,161 A | 1/1963 | Ulrich |
| 3,683,891 A | 8/1972 | Eskridge et al. |
| 4,541,423 A | 9/1985 | Barber |
| 5,755,731 A | 5/1998 | Grinberg |
| 6,443,966 B1 | 9/2002 | Shiu |
| 6,533,749 B1 | 3/2003 | Mitusina et al. |
| 6,949,101 B2 | 9/2005 | McCleary et al. |
| 7,364,582 B2 | 4/2008 | Lee |
| 7,699,846 B2 | 4/2010 | Ryan |
| 7,927,361 B2 | 4/2011 | Oliver et al. |
| 8,007,506 B2 | 8/2011 | To et al. |
| 8,096,957 B2 | 1/2012 | Conquergood et al. |
| 8,162,945 B2 | 4/2012 | Ellis |
| 8,382,742 B2 | 2/2013 | Hermann et al. |
| 8,585,726 B2 | 11/2013 | Yoon et al. |
| 8,920,450 B2 | 12/2014 | Zeroni et al. |
| 2007/0093840 A1 | 4/2007 | Pacelli et al. |
| 2009/0191974 A1 | 7/2009 | Weissenbock et al. |

(Continued)

OTHER PUBLICATIONS

ConMed, Y-Knot Flex All-Suture Anchor System. 2014. [Brochure].
Stryker, ICONIX All Suture Anchor with IntelliBraid Technology. 2012 [Brochure].

*Primary Examiner* — Samuel S Hanna

(57) ABSTRACT

Drill assemblies and methods for drilling into bone are provided. In general, a drill assembly can have a flexible distal portion configured to move between a substantially straight configuration, in which a longitudinal axis of the distal portion is aligned with a longitudinal axis of a proximal shaft portion of the drill assembly, and a curved configuration, in which the longitudinal axis of the distal portion is angularly offset from the longitudinal axis of the proximal shaft portion. The drill assembly can include a proximal shaft, a drill tip, and a plurality of segments located between the proximal shaft and the drill tip. The drill assembly can include a connecting element extending from the proximal shaft, through the segments, and to the drill tip at a distal end of the drill assembly. The drill assembly can include a conformal covering on the distal portion thereof that is configured to curve.

16 Claims, 6 Drawing Sheets

(56) References Cited

U.S. PATENT DOCUMENTS

| | | | |
|---|---|---|---|
| 2012/0172905 A1* | 7/2012 | Lee Shee | A61B 17/1671 606/180 |
| 2013/0261628 A1 | 10/2013 | Burley et al. | |
| 2013/0296864 A1 | 11/2013 | Burley et al. | |
| 2014/0276840 A1* | 9/2014 | Richter | A61B 17/1671 606/80 |
| 2016/0030061 A1* | 2/2016 | Thommen | A61B 17/1671 606/80 |
| 2016/0287264 A1* | 10/2016 | Chegini | A61B 17/1617 |

* cited by examiner

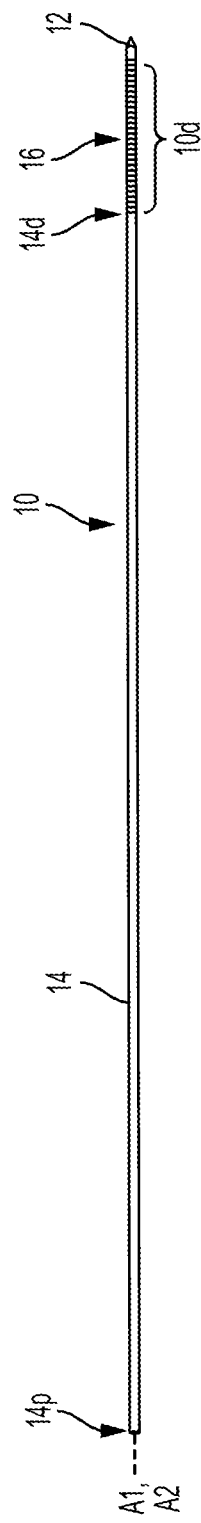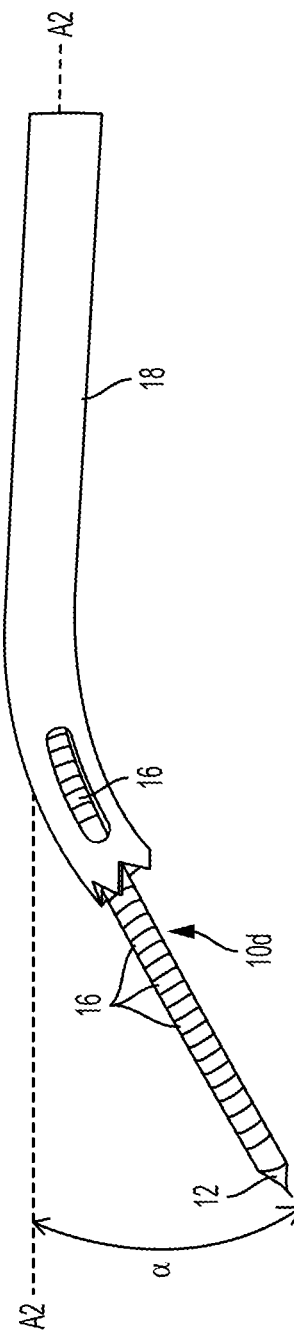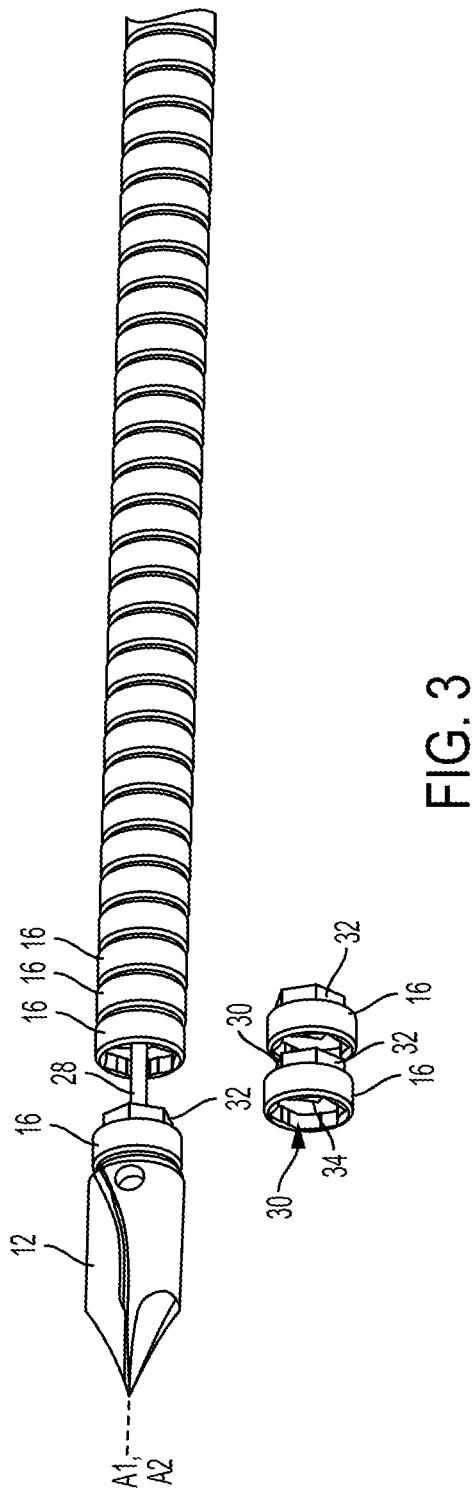
FIG. 1
FIG. 2
FIG. 3

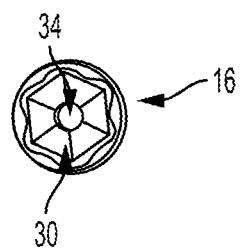
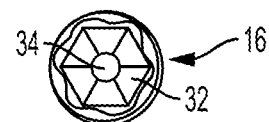
FIG. 4    FIG. 5
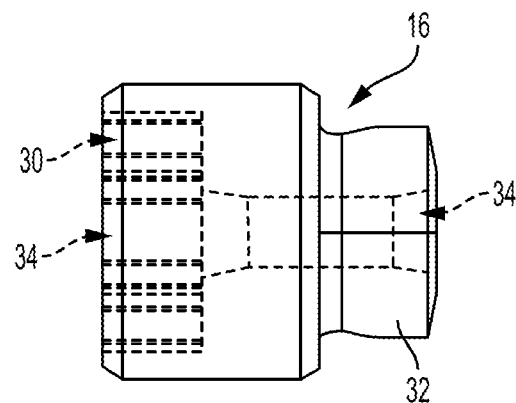
FIG. 6
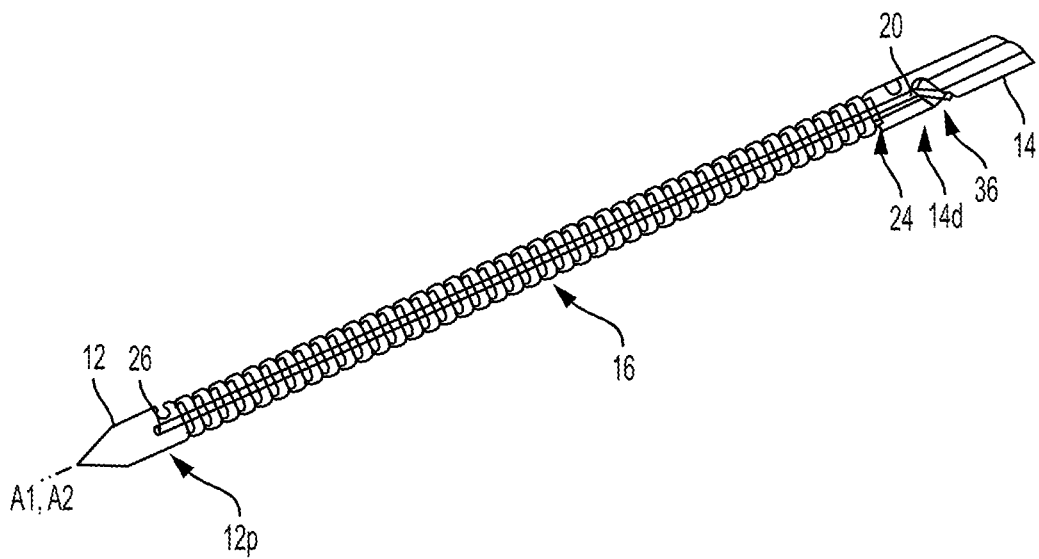
FIG. 7

DRILL ASSEMBLIES AND METHODS FOR DRILLING INTO BONE

FIELD

The present disclosure generally relates to drill assemblies and methods for drilling into bone.

BACKGROUND

A variety of disorders and injuries can require soft tissue repair and suture anchor placement. These procedures often require drilling a hole in bone.

For repair procedures that involve drilling a hole in bone, traditional devices and surgical methods suffer from several drawbacks. For example, variations in anatomy and arthroscopic portal placement can result in undesirable approaches for bone tunneling or anchor placement. Clear access to the optimal bone site can be difficult for certain procedures such as shoulder and hip surgeries. For another example, high stress conditions can result when drilling around a curve. When using a cannulated drill guide, stresses such as compressive forces are applied to a drill, and buckling or lock-up may occur. Also, large offset angles and small bend radii may induce high cyclic bending stresses.

Accordingly, there remains a need for improved devices and methods for drilling into bone.

SUMMARY

In general, drill assemblies and methods for drilling into bone are provided.

In one aspect, a drill assembly is provided that in one embodiment includes a shaft having a longitudinal axis and a distal end. The drill assembly also includes a drill tip disposed distally of the distal end of the shaft, and a plurality of discrete, interconnected segments disposed between the drill tip and the shaft. Each of the segments has a bore extending therethrough. The segments are displaceable with respect to one another such that the segments are configured to move from a substantially linear configuration in which the segments are aligned with the longitudinal axis to a curved configuration with respect to the longitudinal axis when the segments are displaced. The drill assembly also includes a connecting element disposed between the drill tip and the shaft and extending through the bores formed in the segments such that torque is transmitted through the shaft to the drill tip via the segments.

The drill assembly can vary in any number of ways. For example, each segment can have a first mating element disposed on one end of the segment and a second mating element disposed on an opposite end of the segment. The first mating elements can be configured to mate with the second mating elements on adjacent segments. The first mating element can be one of a female receiver and a male member, and the second mating element can be the other of a female receiver and a male member.

In another example, the drill tip can be fixedly attached to the connecting element.

In yet another example, the drill assembly can also include a drill guide. The segments can be at least partially disposed within the drill guide. The segments can be rotatable and translatable within the drill guide. For another example, the shaft can be operatively coupled to an actuator configured to actuate drilling. The torque can be transmitted from the actuator through the shaft to the drill tip via the segments.

The drill guide can vary in any number of ways. For example, the drill guide can include an elongate proximal body having a longitudinal axis and a distal portion that is angled with respect to the longitudinal axis.

In another embodiment, a drill assembly is provided includes a shaft having a longitudinal axis and a distal end. The drill assembly also includes a drill tip disposed distally of the distal end of the shaft, and a flexible element disposed between the drill tip and the shaft. The flexible element is configured to move from a substantially linear configuration aligned with the longitudinal axis to a curved configuration with respect to the longitudinal axis. The drill assembly also includes a conformal covering disposed on the flexible element and configured to reduce diametric expansion of the flexible element due to compressive forces when the flexible element is in the curved configuration and is capable of transmitting bidirectional torque.

The drill assembly can vary in any number of ways. For example, the flexible element and the covering can be configured such that torque is transmitted through the shaft to the drill tip via the flexible element and the covering when the flexible element is in the curved configuration.

For another example, the covering can have an outer surface having at least one helical flute disposed thereon. The at least one helical flute can be oriented to remove material during drilling.

In another example, the flexible element can be a cable including a plurality of wires. The plurality of wires can be twisted around each other in one or more bundles.

For yet another example, the conformal covering can encapsulate the flexible element.

For another example, the drill assembly can include a drill guide. The flexible element having the conformal covering disposed thereon can be at least partially disposed within the drill guide. The flexible element having the conformal covering disposed thereon can be rotatable and translatable within the drill guide. The drill guide can include an elongate proximal body having a longitudinal axis and a distal portion that is angled with respect to the longitudinal axis.

For yet another example, the shaft can be operatively coupled to an actuator configured to actuate drilling.

The conformal covering can include various materials. For example, the conformal covering can include a polymeric material.

In another aspect, a surgical method is provided that in one embodiment includes advancing a drill into a body of a subject through a drill guide having a fixed curvature in a distal portion thereof such that a connecting member of the drill curves within the distal portion of the drill guide. The connecting member includes a plurality of discrete, interconnected segments that are displaceable with respect to one another. The method also includes rotating the drill within the drill guide with the connecting member curved within the drill guide, thereby drilling a hole in a bone of the subject with a drill tip at the distal end of the drill.

The method can have any number of variations. For example, each of the segments can have a bore extending therethrough, and the drill can include a connecting element extending through the bores. The connecting element can have a distal end attached to the drill tip and a proximal end attached to a shaft of the drill such that the torque is transmitted through the shaft to the drill tip via the segments when the drill curves within the distal portion of the drill guide. For yet another example, the shaft can be operatively coupled to an actuator configured to actuate drilling, and the torque can be transmitted from the actuator through the shaft to the drill tip via the segments.

In another example, each segment can have a first mating element disposed on one end of the segment and a second mating element disposed on an opposite end of the segment. The first mating elements can be configured to mate with the second mating elements on adjacent segments.

In another embodiment, a surgical method is provided that includes advancing a drill into a body of a subject through a drill guide having a curvature in a distal portion thereof such that a connecting member of the drill curves within the distal portion. The connecting member includes a flexible element and a conformal covering disposed thereon. The method also includes rotating the drill within the drill guide with the connecting member curved within the drill guide, thereby drilling a hole in the bone of the subject with a drill tip at the distal end of the drill.

The method can vary in any number of ways. For example, the connecting member can be configured to reduce diametric expansion of the flexible element due to compressive forces when the flexible element curves within the distal portion. For another example, the flexible element can be capable of transmitting bidirectional torque. For yet another example, the covering can include at least one helical flute disposed on an outer surface of the covering. For still another example, the flexible element can be a cable including a plurality of wires.

In another aspect, a method of manufacturing a drill assembly is provided that in one embodiment includes applying a coating composition over a flexible element disposed between a drill tip and a shaft to form a conformal covering over the flexible element. The shaft has a longitudinal axis. The flexible element having the conformal covering thereon is configured to be selectively actuated between a substantially linear configuration aligned with the longitudinal axis to a curved configuration with respect to the longitudinal axis. The flexible element having the covering disposed thereon is capable of transmitting unidirectional torque.

The method can have any number of variations. For example, the method can include forming at least one helical flute on a surface of the conformal covering. The at least one helical flute can be formed by injection molding, the at least one helical flute can be oriented to remove material during drilling, and/or the covering can include at least one indent disposed on the surface thereof between the at least one helical flute.

In another example, the method can include attaching the flexible element to the drill tip. In yet another example, the conformal covering can encapsulate the flexible element. For another example, the flexible element can be a cable comprising a plurality of wires. The plurality of wires can be twisted around each other in one or more bundles.

BRIEF DESCRIPTION OF DRAWINGS

This disclosure will be more fully understood from the following detailed description taken in conjunction with the accompanying drawings, in which:

FIG. 1 is a side schematic view of one embodiment of a drill assembly;

FIG. 2 is a side view of a distal portion of the drill assembly of FIG. 1 with a distal portion thereof in a drill guide;

FIG. 3 is a partial exploded perspective view of the drill assembly of FIG. 2;

FIG. 4 is a distal end view of a segment of the drill assembly of FIG. 2;

FIG. 5 is a proximal end view of the segment of FIG. 4;

FIG. 6 is a partial transparent side view of the segment of FIG. 4;

FIG. 7 is a side cross-sectional side view of a distal portion of the drill assembly of FIG. 1 with a connecting element thereof omitted for clarity of illustration;

DETAILED DESCRIPTION

Figure 8:
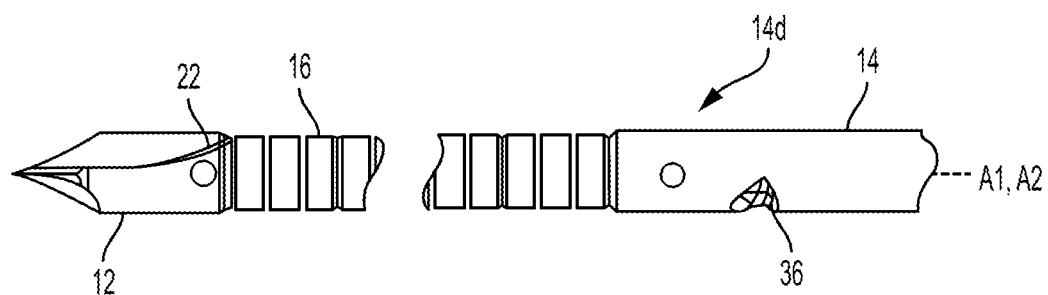
FIG. 8 is a partial side view of the distal portion of the drill assembly of FIG. 7.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary drill assemblies and methods for drilling into bone are provided. In general, a drill assembly can have a flexible distal portion configured to move between a substantially straight or linear configuration, in which a longitudinal axis of the distal portion is aligned with a longitudinal axis of a proximal shaft portion of the drill assembly, and a curved configuration, in which the longitudinal axis of the distal portion is angularly offset from the longitudinal axis of the proximal shaft portion. A person skilled in the art will appreciate that the flexible distal portion may not be precisely linear or straight but nevertheless be considered to be substantially linear or straight due to any one or more factors, such as manufacturing tolerances of the drill assembly and/or sensitivity of measurement equipment. The drill assembly being able to move between the substantially straight and curved configurations may help compensate for a surgeon's unsatisfactory angle of approach to a target surface of a target to be drilled, such as a surface of a bone, since the drill assembly can curve to be desirably positioned relative to the target site to drill at a desired angle into the target surface, e.g., to be positioned perpendicular to the target surface to drill into the target. The drill assembly being able to move between the substantially straight and curved configurations may allow the drill assembly to be inserted into a patient's body and drilled into tissue cavities while in the curved configuration to bypass tissue structures and thereby avoid damaging the tissue structures while still being effective for drilling. The drill assembly being able to move between the substantially straight and curved configurations may allow a surgeon to not switch drill assemblies during performance of a surgical procedure since the same drill assembly can be used to form linear holes and curved holes, which may save time and/or reduce instrument clutter in an operating room.

The drill assembly can include a proximal shaft, a drill tip, and a plurality of segments located between the proximal shaft and the drill tip. The drill assembly can also include a connecting element extending from the proximal shaft, through the segments, and to the drill tip at a distal end of the drill assembly. The connecting element can be flexible so as to be able to bend and facilitate the curving of the drill assembly's distal portion. The connecting element can be configured to hold the segments together under a compressive load and thereby facilitate transmission of torque from one segment to the segment directly distal thereto, which may facilitate stable, effective drilling of the drill assembly (e.g., the drill tip and at least some of the segments) into a target regardless of whether the drill assembly's distal portion is in the substantially straight configuration or the curved configuration.

A drill assembly including a flexible distal portion can include a conformal covering on the distal portion thereof that is configured to curve. The conformal covering can be configured to reduce diametric expansion of the distal portion due to compressive forces when the distal portion is in the curved configuration and the distal portion is capable of transmitting bidirectional torque.

The drill assemblies described herein can be configured to be advanced to a target site through a cannulated drill guide. The drill guide can have a curved distal portion that causes the distal portion of the drill assembly to curve, e.g., move from the substantially straight configuration to the curved configuration, when advanced therethrough. The drill assembly can thus be configured to passively bend. A drill guide having a particular distal curvature may be selected for use with the drill assembly to allow the drill assembly to curve at a particular angle as appropriate for the particular surgical procedure being performed and/or for the particular anatomy of the patient on which the drill assembly is used. A plurality of drill guides can be provided as a kit, with each of the drill guides having a different distal curvature, thereby allowing a surgeon to select a one of the drill guides for use with the drill assembly as desired for a particular application. The drill assembly can be provided as part of the kit.

The drill assemblies described herein can be used in various surgical procedures including, for example, hip arthroscopy and shoulder arthroscopy.

FIG. 1 illustrates one embodiment of a drill assembly 10. As shown, the drill assembly 10 includes a drill tip 12, an elongate shaft 14, and a plurality of segments 16 located between the drill tip 12 and the shaft 14. A flexible distal portion 10d of the drill assembly 10 defined by the segments 16 is configured to move between a substantially straight or linear configuration, in which a longitudinal axis A1 of the distal portion 10d is aligned with a longitudinal axis A2 of the shaft 14, and a curved configuration, in which the longitudinal axis A1 of the distal portion 10d is angularly offset from the longitudinal axis A2 of the shaft 14. The distal portion 10d is shown in the straight configuration in FIG. 1 and in the curved configuration in FIG. 2 with the distal portion 10d at an angle α relative to the shaft 14. FIG. 2 also shows a cannulated drill guide 18 through which the drill assembly 10 has been advanced such that the drill tip 12 and a partial number of the segments 16, including segments 16 immediately proximal to the drill tip 12, are located distally beyond a distal end 18d of the drill guide 18.

The shaft 14 defines a proximal portion of the drill assembly 10. The shaft has a distal end 14d and a proximal end 14p that define the longitudinal axis A2 therebetween. The shaft 14 is rigid and maintains a straight longitudinal axis A2. The shaft 14 has a blind hole 20 in a distal end thereof, as shown in FIG. 7. The shaft 14 can have a variety of sizes, shapes, and configurations. The shaft 14 generally a cylindrical shape and a circular cross-sectional shape in this illustrated embodiment, but the shaft 14 can have a variety of other shapes. For example, the shaft 14 can have another shape, such as an elliptical cross-sectional shape, a cone shape, a triangular prism shape, etc.

As shown in FIG. 7, the shaft 14 includes an anti-rotation feature 24. The anti-rotation feature 24 is configured to prevent the shaft 14 from rotating relative to the segments 16 and the drill tip 12 during drilling when the drill assembly 10 is rotating with the shaft 14 rotating about its longitudinal axis A2 and the segments 16 and the drill tip 12 rotating about the distal portion's longitudinal axis A1, which may be straight or curved during drilling. The anti-rotation feature 24 may thus enable torque transfer between the shaft 14 and the segments 16 and the drill tip 12. The anti-rotation feature 24 can be configured to mate with a proximal-most one of the segments 16, as discussed further below. The anti-rotation feature 24 can have a variety of sizes, shapes, and configurations. The anti-rotation feature 24 is a female hex in this illustrated embodiment but can have other configurations, such as a male hex or a spline.

The drill tip 12 defines a distal tip of the drilling assembly 10. The drill tip 12 is configured to lead the drilling assembly into a target (such as a bone) to be drilled, as will be appreciated by a person skilled in the art. The drill tip 12 can have a variety of sizes, shapes, and configurations. As shown in FIGS. 1-3 and 7-9, the drill tip 12 tapers distally to a point, which may facilitate penetration of the drill tip 12 into a target to be drilled.

Figure 9:
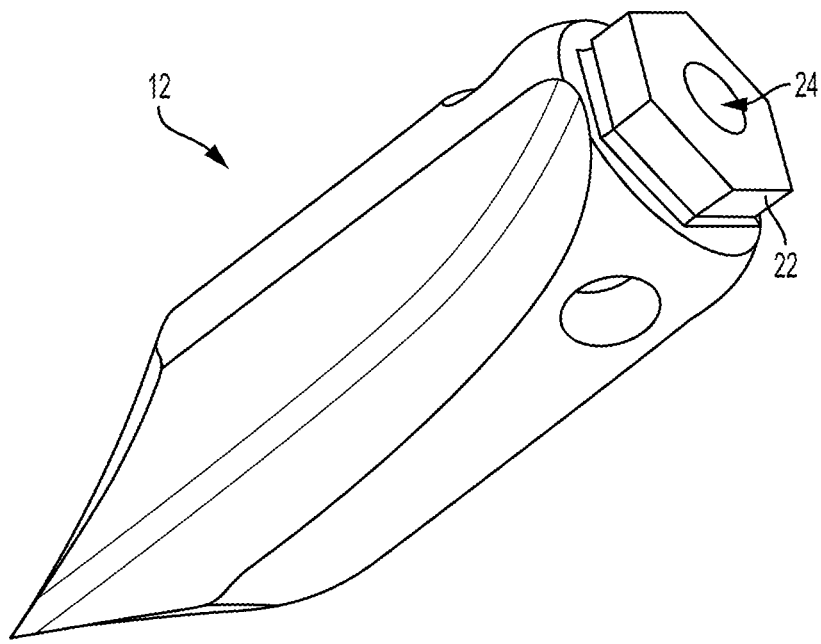
FIG. 9 is a perspective view of a drill tip of the drill assembly of FIG. 1.

As shown in FIG. 9, the drill tip 12 includes an anti-rotation feature 22. The anti-rotation feature 22 is configured to prevent the drill tip 12 from rotating relative to the segments 16 and the shaft 14 during drilling when the drill assembly 10 is rotating with the shaft 14 rotating about its longitudinal axis A2 and the segments 16 and the drill tip 12 rotating about the distal portion's longitudinal axis A1, which may be straight or curved during drilling. The anti-rotation feature 22 may thus enable torque transfer between the drill tip 12 and the segments 16 and the shaft 14. The anti-rotation feature 22 can be configured to mate with a distal-most one of the segments 16, as discussed further below. The anti-rotation feature 22 can have a variety of sizes, shapes, and configurations. The anti-rotation feature 22 is a male hex in this illustrated embodiment but can have other configurations, such as a female hex or a spline.

The segments 16 are discrete, interconnected elements disposed between the distal drill tip 12 and the proximal shaft 14. The segments 16 collectively define the flexible distal portion 10d of the drilling assembly 10. FIGS. 4-6 show one of the segments 16 as a standalone element. Each of the segments 16 is the same as one another. In other embodiments, one or more of the segments 16 can be different from one or more of the other segments 16. For example, a distal-most one of the segments 16 can have a different configuration from a remainder of the segments 16 to facilitate attachment thereof to the drill tip 12, a proximal-most one of the segments 16 can have a different configuration from a remainder of the segments 16 to facilitate attachment thereof to the shaft 14, and/or segments can have different diameters with the diameters of the segments 16 decreasing from a proximal end of the distal portion 10d to a distal end of the distal portion 10d, with the distal-most one of the segments having the smallest diameter and the proximal-most one of the segments 16 having the largest diameter.

Each segment 16 is interconnected with the segment(s) 16 immediately adjacent thereto 16. The distal-most one of the segments 16 is interconnected with one of the segments 16 and with the drill tip 12, the proximal-most one of the segments 16 is interconnected with one of the segments 16 and the shaft 14, and a remainder of the segments 16 (generally referred to as "intermediate segments") are each interconnected with two of the segments 16.

The segments 16 can be interconnected with an adjacent segment 16 in any of a number of ways. As shown in FIGS. 3-6, each segment 16 has a first mating element 30 on a distal end thereof and a second mating element 32 disposed on a proximal end thereof. The first mating elements 30 are in the form of a female hex socket, and the second mating element 32 is in the form of a male hex protrusion configured to be received within the female socket of the first mating element. The first mating element 30 of each of the intermediate segments is configured to mate with the second mating element 32 of the one of the segments 16 proximal thereto. The first mating element 30 of the distal-most segment 16 is configured to mate with the anti-rotation feature 22 of the drill tip 12, which is in the form of a male protrusion configured to be received in the female socket of the first mating element 30. The second mating element 32 of the proximal-most segment 16 is configured to mate with the anti-rotation feature 24 at the distal end of the shaft 14, which is in the form of a female socket, as shown in FIG. 7. The first and second mating elements 30, 32 are configured to facilitate mating and to facilitate anti-rotation, namely to prevent the segments 16 from rotating relative to the shaft 14 and the drill tip 12 during drilling when the drill assembly 10 is rotating with the shaft 14 rotating about its longitudinal axis A2 and the segments 16 and the drill tip 12 rotating about the distal portion's longitudinal axis A1, which may be straight or curved during drilling. The anti-rotation features 22, 24, 30, 32 that mate together can be provided with clearance to enable torque transmission when any of the segments 16 become anti-linear or off-axis during curvature of the distal portion 10d.

Although the first mating elements 30 are female sockets and the second mating elements 32 are male protrusions in this illustrated embodiment, in another embodiment, the first and second mating elements 30, 32 can have other configurations. For example, the first mating elements 30 can be male hex protrusions and the second mating elements 32 can be female hex sockets, with the drill tip 12 and the shaft 14 also being modified to mate with these mating elements. For another example, the first and second mating elements 30, 32 can include splines, with the drill tip 12 and the shaft 14 also being modified to mate with these mating elements. For yet another example, one of the first and second mating elements 30, 32 can include a ball and the other of the first and second mating elements 30, 32 can include a spherical socket configured to seat the ball of an adjacent segment (or the adjacent drill tip 12 or shaft 14) therein. Other examples of the first and second mating elements 30, 32 include a hinge joint, pin-and-cup joint, and a conically tapered joint.

The segments 16 are configured to be displaceable with respect to one another such that the segments 16 are configured to move from a substantially linear configuration, in which the distal portion 10d is in the substantially linear configuration and the segments 16 are aligned with the longitudinal axis A2 of the shaft 14, to a curved configuration, in which the distal portion 10d is in the curved configuration and the segments 16 are displaced and are curved with respect to the longitudinal axis A2 of the shaft 14. The angle α (see FIG. 2) at which the distal portion 10d in the curved configuration can be, for example, a non-zero angle up to about 90°, in a range of about 60° to 90°, in a range of about 25° to 90°, in a range of about 25° to 60°, or a non-zero angle up to about 60°. The drill assembly 10 can thus, for example, be configured to drill at an angle in a range of 0° to about 90°, in a range of about 60° to 90°, in a range of about 25° to 90°, in a range of about 25° to 60°, or a range of 0° about 60°. A person skilled in the art will appreciate that the angle α may not be precisely at an angular measurement, e.g., precisely at 90°, but nevertheless to considered to be at about that angular measurement due to any one or more factors, such as manufacturing tolerances and/or sensitivity of measurement devices. The angle α may be constrained to a maximum value by the curvature of the drill guide 18 through which the drilling assembly 10 passes and/or by the dimensions of a cannula or other access device through which the drill guide 18 is advanced to enter a patient's body. Curvature is a strong driver of stress, with increasing stresses resulting from an increased radius of curvature, so strength provided by a connecting member 28 of the drill assembly 10, which is discussed further below, may help compensate for these stresses.

When the segments 16 are not displaced, e.g., when the distal portion 10d is in the linear configuration, the first and second mating elements 30, 32 of the segments 16 are in their fully mated positions with the segment(s), drill tip 12, and/or shaft 14 to which they are mated. When the segments 16 are displaced, e.g., when the distal portion 10d is in the curved configuration, at least some of the first and second mating elements 30, 32 of the segments 16 are moved from their fully mated positions with the segment(s), drill tip 12, and/or shaft 14 to which they are mated to be partially mated thereto, thereby allowing for the curvature. Thus, the segments 16 are in one orientation with respect to each other in the curved configuration and in another orientation with respect to each other in the linear configuration.

The first and second mating elements 30, 32 can be configured to enable a finite angular displacement from the longitudinal axis A1 of the distal portion 10d, which can also be a longitudinal axis of a connecting element 28, discussed further below. For example, the second mating elements 32 in the form of the male protrusion can be curved to enable displacement while being configured to transmit torque between itself and the first mating element 30 mated thereto.

The segments 16 can have any of a variety of dimensions. A size of the segments 16 may vary depending on the intended application of the drilling assembly 10, and the overall drill assembly 10 dimensions may be a function of a total number of the segments 16 and the size of the individual segments 16. In an exemplary embodiment, each of the segments 16 can have a longitudinal length in a range of about 0.5 to 5 mm, such as about 1.5 mm, and a maximum diameter of each of the segments 16 can be in a range of about 1 to 10 mm, such as about 2 mm. A total length of the segments 16, e.g., a length of the distal portion 10d, can be in a range of about 1 to 2 in.

The portions of the segments 16 exposed externally when mated together to form the flexible distal portion 10d are cylindrical with circular cross-sectional shapes. The distal portion 10d thus has a cylindrical shape with a circular cross-sectional shape, which may facilitate advancement thereof through a drill guide, which traditionally have cylindrical cannulated pathways therethrough. The segments 16 can, however, have other shapes. The segments 16 can have virtually any shape that enables one segment 16 to mate with an adjacent segment 16 to form the flexible distal portion 10d. Examples of suitable shapes include conical, spherical, and cuboid.

The segments 16 can each be made from any of one or more biologically compatible materials, such as metals (e.g., surgical grade titanium, etc.) and polymers (e.g., poly-ether-ether-ketone (PEEK), polylactic acid, and polyglycolic acid). In an exemplary embodiment, the segments 16 can be rigid, with their interconnection allowing for the flexibility of the flexible distal portion 10d. Different ones of the segments 16 can be made from different materials to provide distinct advantages tailored to each segment 16, e.g., allowing certain portions of the distal portion 10d to be more rigid that others, such as being more rigid toward the distal end thereof to facilitate secure drilling.

As shown in FIGS. 3-6, each of the segments 16 includes a bore 34 extending longitudinally therethrough. The bores 34 are configured to receive the connecting element 28 therein such that the connecting element 28 extends through all of the segments 16. The bores 34 are centrally located so as to be coaxial with the longitudinal axis A1, thereby allowing the connecting element 28 to extend centrally through the distal portion 10d, which may help provide structural support thereto and/or facilitate even torque transmission. In another embodiment, individual segments 16 can have bores 34 that are not coaxial to the longitudinal axis A1 to create fixed curving of the drill assembly 10 such that the drill assembly 10 does not have a substantially linear configuration but is instead configured to move between the fixed curvature configuration to another curved configuration. As such, when the segments 16 are engaged with adjacent segments 16, the off-axis bores 34 can form an off-axis internal cannulation where the connecting element 28 can exert a tensile force onto the drill assembly 10 to thereby curve the distal portion 10d to an off-axis direction. In another embodiment, the segments 16 can be off-axis so as to be tilted relative to one another to bring the individual segments 16 off axis with respect to one another. For example, the second mating element 32 of a segment 16 can be positioned out of alignment with respect to an adjacent segment's first mating element 30, and as such, the segment 16 is tilted towards one direction. This construction enables the drill assembly 10 to form a fixed curved construct for use in forming (e.g., drilling) a curved hole. For example, the drill assembly 10 can be inserted into a curved drill guide, and when a tensile forced is applied, e.g., by actuating an actuator coupled to the drill assembly 10, the segments 16 can be tilted to curve while assuming a substantially rigid configuration inside the drill guide.

As mentioned above and as shown in FIG. 3, the drill assembly 10 includes the connecting element 28 that extends through the drilling assembly's flexible distal portion 10d within the bores 34 of the segments 16. In general, the connecting element 28 is a flexible member configured to facilitate attachment of the drill tip 12, segments 16, and shaft 14 and to facilitate torque transmission between adjacent segments 16.

The connecting element 28 can have a variety of sizes, shapes, and configurations. Generally, the connecting element 28 has an elongate shape and is in the form of a wire, cable, filament, shaft, or coil. The connecting element 28 can have any longitudinal length, which is longer than the distal portion 10d in order to facilitate passage of the connecting element 28 proximally and distally beyond the distal portion 10d. For example, the connecting element 28 can have a longitudinal length in a range of about 1 to 2 inches. The longitudinal length of the connecting element 28 can be based on a desired depth of hole to be drilled using the drill assembly 10 and on an amount of curve in the drill guide and/or cannula through which the drill assembly 10 is advanced.

The connecting element 28 being flexible allows the connecting element 28 to bend during movement of the flexible distal portion 10d of the drill assembly 10 between the substantially linear and curved configurations. The connecting elements 28 can thus be configured to move between a substantially linear configuration in which a longitudinal axis of the connecting element 28 is aligned with the longitudinal axis A2 of the shaft and a curved configuration in which the longitudinal axis of the connecting element 28 is angled at the angle $\alpha$ with respect to the longitudinal axis A2 of the shaft 14. The connecting element 28 can be configured to flex side-to-side but not up-and-down, which may facilitate drilling. The connecting element 28 can thus be configured as a tensile member having lateral compliance.

The connecting element 28 has a distal end seated in the blind hole 26 of the drill tip 12, a proximal end seated in the blind hole 20 of the shaft 14, and an intermediate portion between the proximal and distal ends thereof that extends through the bores 34 of the segments 16. The connecting element 28 can be fixedly attached to the drill tip 12 in the blind hole 26 thereof and to the shaft 14 in the blind hole 20 thereof, which may facilitate structural stability of the drill assembly 10 and/or torque transmission along the distal portion 10d. The connecting element 28 can be fixedly attached to the drill tip 12 and the shaft 14 in any of a variety of ways, such as by welding, soldering, swaging, adhesive connection, or crimping. The shaft 14 can include a side opening 36 (see FIGS. 7 and 8) configured to facilitate fixed attachment of the connecting element 28 thereto by allowing the connecting element 28 to be pulled therethrough and held under compression during attachment of the connecting element 28 to the shaft 14 within the blind hole 20. The connecting element 28 can also be fixedly attached to each one of the segments 16, such as by welding, soldering, swaging, adhesive connection, or crimping, which may facilitate structural stability of the drill assembly 10 and/or torque transmission along the distal portion 10d. The connecting element 28 being fixedly attached to the segments 16 may prevent the segments 16 from translating laterally relative to one another, which may facilitate smooth curvature and/or smooth passage of the distal portion 10d through the drill guide 18.

The connecting element 28 is configured to provide a compressive load on the segments 16 to hold the segments 16 together. The connecting element 28 is configured to maintain a permanent axial connection between the segments 16. The connecting element 28 is thus configured to keep the segments 16 in contact with each other when the connecting member 28 is curved during use, e.g., when the distal portion 10d is in the curved configuration. The connecting element 28 can thus apply a compressional force to the drill assembly 10 to cause all of the segments 16 to move toward one another and form a substantially rigid configuration in which the drill assembly 10 can drill when in the curved configuration and not buckle within the drill guide 18.

The connecting element 28 is a single unitary member, which may facilitate manufacturing and/or structural stability of the connecting element 28, but the connecting element 28 can instead be formed of one or more parts, which may increase flexibility of the connecting element 28. In one embodiment, the connecting element 28 can be in the form of a plurality of discrete, interconnected segments similar to that discussed herein regarding the segments 16.

The connecting element 28 can be made from any one or more materials, such as any of those discussed above regarding the segments 16. One or more of these materials can also be used to form the drill tip 12 and the shaft 14.

The shaft 14 is fixedly attached to the segments 16 and the drill tip 12 in this illustrated embodiment, e.g., fixed thereto via the connecting element 28. In other embodiments, the shaft 14 can be removably attached to the segments 16 and the drill tip 12. The shaft 14 being configured to be removed from the segments 16 and the drill tip 12 may facilitate cleaning post-use. The shaft 14 being configured to be removed from the segments 16 and the drill tip 12 may allow the shaft 14 to be selectively connected to drill assembly distal portions including different numbers and/or sizes of segments and/or to drill assembly drill tips of different sizes, which may facilitate re-use of the shaft 14 in a same surgical procedure and/or in subsequent surgical procedures by allowing the portion of the drill assembly 10 that is drilled into a target, such as drilled into bone, to be selected as desired by a surgeon (e.g., in accordance with a size of a hole to be drilled).

The shaft 14 can be operatively coupled to an actuator (not shown) configured to actuate drilling, such as any of a number of drill controls, as will be appreciated by a person skilled in the art. The drilling causes the shaft 14, drill tip 12, and segments 16 to rotate about their respective axes A1 (drill tip and segments 16), A2 (shaft 14). A speed of the rotation, e.g., about 1200 RPM, is limited by the drilling instrument, as will be appreciated by a person skilled in the art. Torque can be transmitted from the actuator through the shaft 14 to the drill tip 12 via the segments 16.

In mentioned above, the drill assembly 10 can be configured to be advanced through a drill guide. Any of a variety of types of drill guides may be used, as will be appreciated by a person skilled in the art, such as the drill guide 18 of FIG. 2. As shown in FIG. 2, the drill guide 18 includes an elongate proximal portion having a longitudinal axis, which is the same as the shaft's axis A1 as illustrated, and a distal portion having a longitudinal axis, which is the same as the flexible distal portion's axis A1 as illustrated, that is angled with respect to the longitudinal axis of the elongate proximal portion. The drill guide's distal portion can be at any angle with respect to the drill guide's proximal portion, including at a zero angle in which case the drill guide is not curved as is configured to maintain the drill assembly 10 advanced therethrough in the substantially linear configuration. The drill guide 18 has a circular cross-sectional shape but can have another cross-sectional shape, which may correspond to the drill assembly's cross-sectional shape in at least the distal portion 10d thereof. A size of the drill guide 18 can be proportional to a diameter of an implant (e.g., in a range of about 1.7 to 2.3 mm, etc.) to be implanted in a hole drilled by the drill assembly 10.

The drill guide 18 has a distal end configured to engage bone or other tissue structures. The drill guide 18 has one or more fenestrations at its distal end. Debris (e.g., bone bits, etc.) may exit the drill guide 18 through the fenestrations as the drill assembly 10 bores into bone.

A drill assembly including a flexible distal portion located between a shaft of the drill assembly and a drill tip of the drill assembly can include a conformal covering (also referred to herein as a "conformal coating" and a "shell") disposed on a flexible member in the flexible distal portion. The flexible distal portion is configured to move between a substantially straight or linear configuration and a curved configuration, as discussed herein. The flexible member includes a cable that has a plurality of wires twisted or braided together. The flexible member is configured to withstand various forces and stresses. For example, the flexible member can be configured to transmit torque during drilling because the wires are oriented in the same direction as principal stresses as they are placed under load, e.g., as the flexible member is rotated in a preferred direction. The flexible member tends to expand when rotated in a non-preferred direction, e.g., in a direction opposite to the wires' twisting or braiding. The conformal covering may reduce diametric expansion of the flexible member due to compressive forces when the flexible distal portion is in the curved configuration, may resist diametrical expansion of the flexible member when torsional loading is reversed in direction, and may counteract the compression associated with bi-directional torsion and accordingly minimize buckling. In other words, the expansion of the flexible member when rotated in the non-preferred direction increases a diameter of the flexible member, which may cause the flexible member to get stuck or jammed within a drill guide and/or other introducer device in which the flexible distal portion is positioned. The conformal coating may reduce this expansion of the flexible member and thus reduce chances that the flexible member will get stuck or jammed within the drill guide (and/or other introducer device) and ultimately fail and/or may allow a surgeon to drill far off-axis because the flexible member and conformal coating are laterally compliant.

The wires of the flexible member can be sized such that the bending stresses resulting from an off-axis approach are well below the yield strength of the material (smaller wires result in lower bending stresses). Torsional strength may be improved by orientation of the wires in the direction of the principal stresses.

Figure 10:
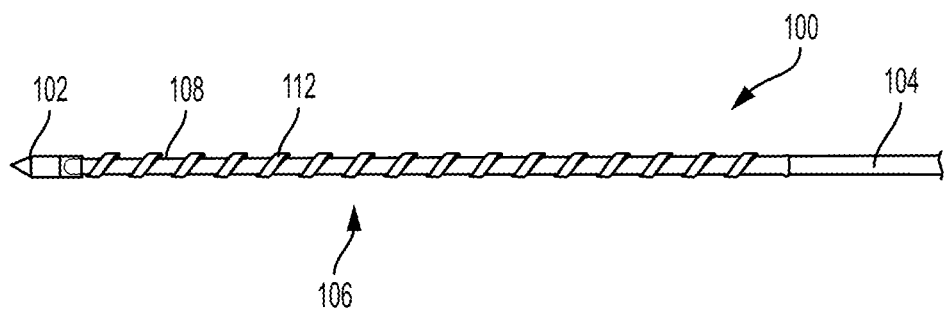
FIG. 10 is a side view of a distal portion of another embodiment of a drill assembly.
Figure 11:
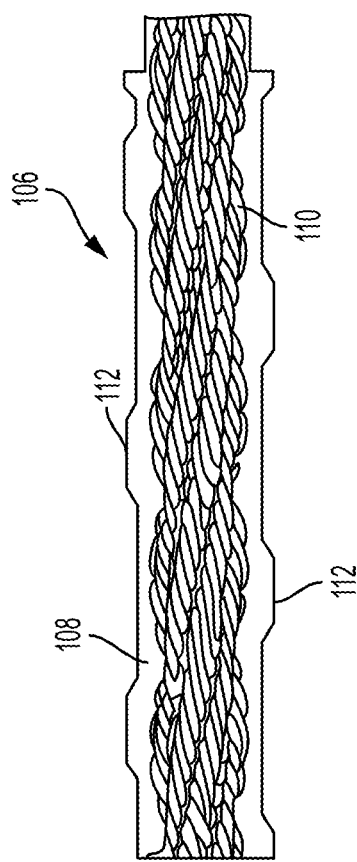
FIG. 11 is a partial cross-sectional side view of a portion of the distal portion of the drill assembly of FIG. 10.

FIGS. 10 and 11 illustrate one embodiment of a drill assembly 100 that includes a drill tip 102, an elongate shaft 104 (FIG. 10 only shows a distal portion of the shaft 104), and a flexible distal portion 106 extending between the drill tip 102 and the shaft 104. The flexible distal portion includes a flexible member 110 and a conformal coating 108 disposed on the flexible member 110. The drill assembly 100 is configured to be advanced through a drill guide to a target for drilling, as discussed herein.

The drill tip 102 can have a variety of sizes, shapes, and configurations. In general, the drill tip 102 can be configured similar to that discussed above regarding the drill tip 12 of the drill assembly 10 of FIG. 1.

The shaft 104 can have a variety of sizes, shapes, and configurations. In general, the shaft 104 can be configured similar to that discussed above regarding the shaft 14 of the drill assembly 10 of FIG. 1. The shaft 104 can be fixedly or removably attached to the flexible member 110 and the drill tip 102, also similar to that discussed above regarding the drill assembly 10 of FIG. 1.

The flexible member 110 can have a variety of sizes, shapes, and configurations. As shown in FIG. 11, the flexible member 110 includes a plurality of wire strands twisted together, with each of the strands including a plurality of wires twisted together. The flexible member 110 can be made from any one or more materials, such as at least one polymeric material. The flexible member 110 can be fixedly attached to the drill tip 102 and the shaft 104 similar to that discussed above regarding the connecting member, e.g., a distal end of the flexible member 110 can be disposed in a blind hole at a proximal end of the drill tip 102 and a proximal end of the flexible member 110 can be disposed in a blind hole at a distal end of the shaft 104. If welded in a blind hole of either the drill tip 102 or the shaft 104, the wires of the flexible member 110 can be penetrated by the weld.

The conformal coating 108 can have a variety of sizes, shapes, and configurations. In general, the conformal coating 108 includes a thin layer of flexible material configured to conform to the flexible member 110 that the coating 108 surrounds. The conformal coating 108 can be made from any one or more materials, such as a lubricious and biologically inert material such as PEEK or other polymer. A lubricious and biologically inert material may provide bearing support against cannulated/non-cannulated instruments, thereby minimizing debris generation (e.g., the material will not flake off as the flexible distal portion including the coating 108 is advanced through a fixed curve of a drill guide), and associated adverse toxicological response associated with debris, particularly metallic or bioactive debris. The conformal coating 108 can include a solvent in addition to a polymer.

The conformal coating 108 includes one or more surface features 112 thereon configured to facilitate material removal because drilled away bits of material (e.g., bits of bone) can spiral along an outside of the conformal coating 108 and be pulled out or otherwise removed easily from a body of a patient on which the drill assembly 100 is being used. The one or more surface features 112 can have a variety of sizes, shapes, and configurations. In this illustrated embodiment, the one or more surface features 112 includes a helical flute. The helical flute adds material thickness that provides additional compression-resistance to the flexible member 110. The helical flute is oriented opposite to the helical direction of the wire strands, which may facilitate the ejection of drilled debris material and/or help prevent buckling of the flexible member 110 under compression. The angle of the helix is about 45° to maximize tensile strength, although other angles are possible.

Other examples of the one or more surface features include indents or bosses. The one or more indents can be positioned between valleys of the helical flute or can be similarly positioned if the drill assembly 100 does not include the helical flute. The one or more indents may enable the conformal coating 108 to support the flexible member 110 during a molding process, discussed below, define the a spacing between flutes of the helical flute, and maintain the orientation of the flexible member 110 within the conformal coating 108. In at least some embodiments, the shell 108 does not include any surface features.

The conformal coating 108 is disposed on an entirety of the inner flexible member 110 so as to extend along an entirety of the distal portion 106, which may reduce diametric expansion of the flexible member 110 due to compressive forces when in the curved configuration along the entire length of the flexible member 110. In another embodiment, the conformal coating 108 can be on only a partial portion of the inner flexible member 110. For example, the conformal coating 108 can be on only a distal portion of the flexible member 110, which may help prevent buckling closest to the drill tip 102 where stability of the drill assembly 100 may be more important during drilling. A minimum length of the flexible member 110 and the shell 108 thereon can be, for example, a length of the nonlinear cannulation and intended bone tunnel depth minus a length of the drill tip.

The conformal coating 108 can be applied to the flexible member 110 in various ways such as, for example, injection molding, overmolding, spraying, or dipping a coating composition thereon. After the coating composition is applied, the composition can be dried to form the conformal coating 108. The coating composition can be dried in any of a variety of ways, such as by evaporation or heating. When the conformal coating 108 is applied to the flexible member 110, the material of the conformal coating 108 can penetrate or migrate between individual wires of the flexible member 110 prior to drying and thereby reduce any unsupported length of individual wires. In other words, the conformal coating 108 can conform to the micro-structure of the flexible member 110, which may minimize unsupported areas of the flexible member 110, such as a braided cable or wires, and maximize bi-directional torque capability. Because the conformal coating 108 is generally fixed and interlocked against the flexible member 110, the conformal coating 108 contributes to the torsional strength along with the flexible member 110.

The helical flute can be formed in any of a variety of ways, such as by machining or injection molding.

Before or after disposed the conformal coating 108 on the flexible member 110, the flexible member 110 can be attached to the drill tip 102 and shaft 104.

Figure 12:
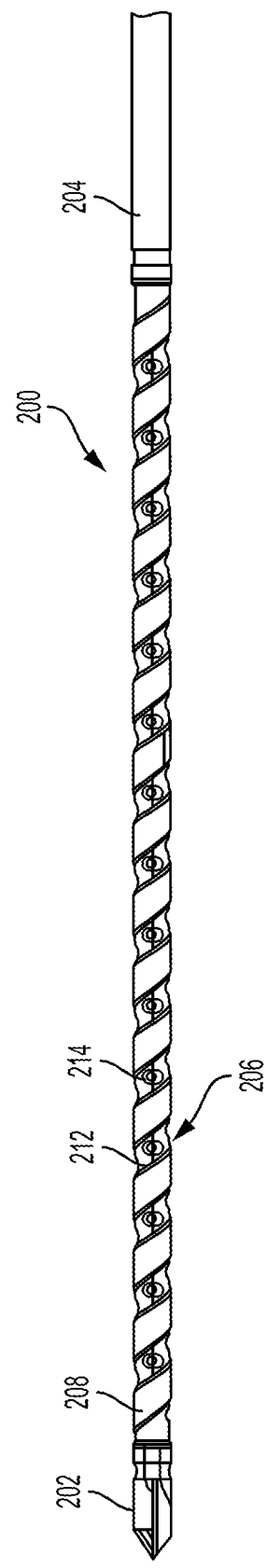
FIG. 12 is a side view of a distal portion of another embodiment of a drill assembly.
Figure 13:
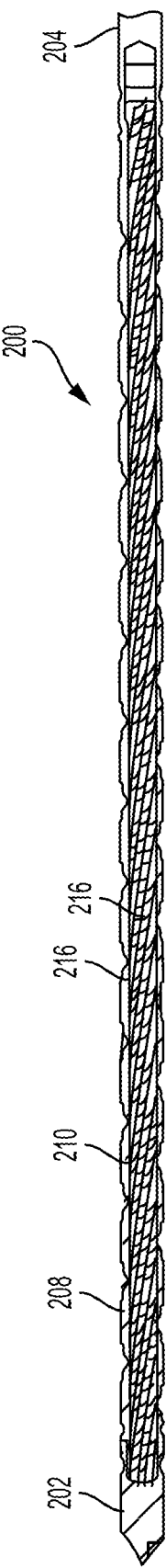
FIG. 13 is a cross-sectional view of the distal portion of the drill assembly of FIG. 12.
Figure 14:
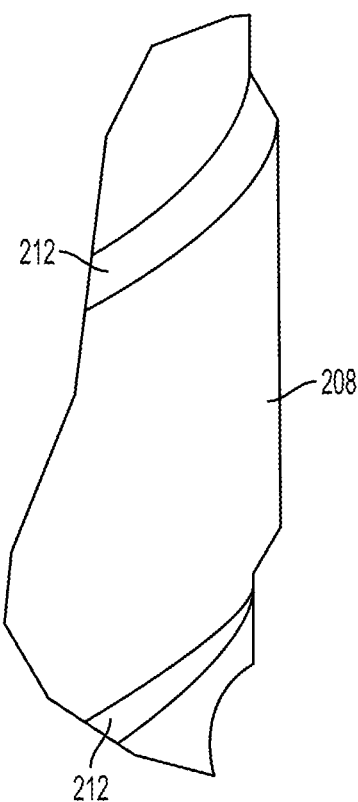
FIG. 14 is a partial side view of a portion of the drill assembly of FIG. 12.
Figure 15:
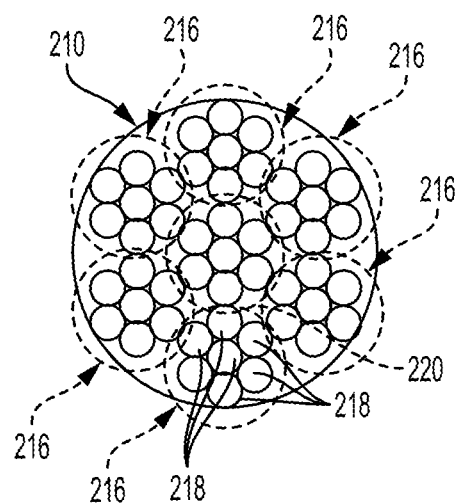
FIG. 15 is a cross-sectional end view of a flexible member of the drill assembly of FIG. 12.

FIGS. 12-14 illustrate another embodiment of a drill assembly 200 that includes a drill tip 202, an elongate shaft 204 (FIGS. 12 and 13 that show the shaft 204 only shows a distal portion thereof), and a flexible distal portion 206 extending between the drill tip 202 and the shaft 204 and including a flexible member 210 having a conformal coating 208 disposed thereon. The drill assembly 200 is generally configured and used similar to the drill assembly 100 of FIGS. 10 and 11. As shown in FIGS. 12 and 14, the drill assembly 200 includes one or more surface features in the form of a helical flute 212 and a plurality of indents or bosses 214 located within the valleys of the helical flute 212. As shown in FIGS. 13 and 15, the flexible member 210 includes a plurality of wire strands 216 twisted together, with each of the strands 216 including a plurality of wires 218 twisted together, and a central core 220 that includes a plurality of wires twisted together.

Figure 16:
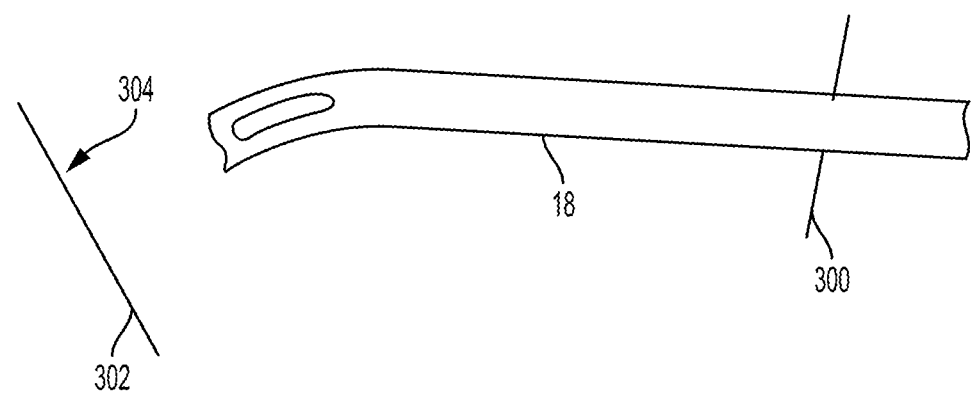
FIG. 16 is a side view of the drill guide of FIG. 2 with advanced through skin.
Figure 17:
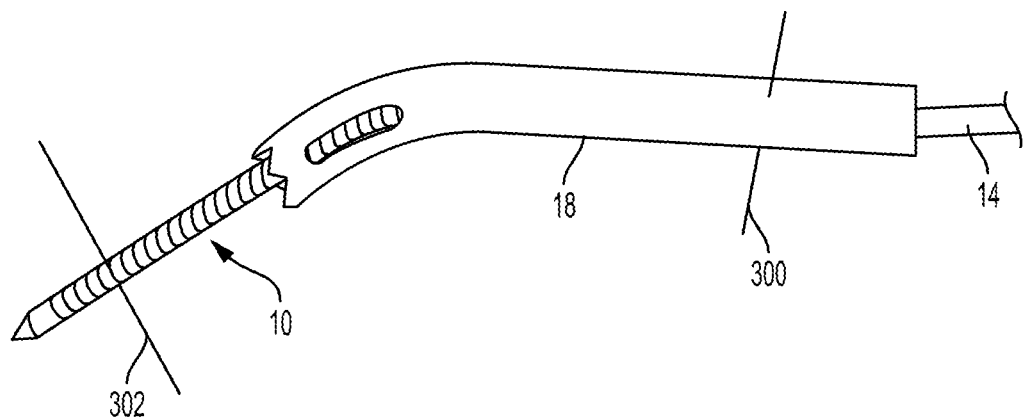
FIG. 17 is a side view of the drill assembly of FIG. 1 advanced through the drill guide of FIG. 16 and drilled into a bone.

One embodiment of drilling using a drill assembly is illustrated in FIGS. 16 and 17. Although the method of FIGS. 16 and 17 is illustrated with respect to the drill assembly 10 of FIG. 1 and the drill guide 18 of FIG. 2, any of the drill assemblies and any of the drill guides described herein can be similarly used. Although the method of FIGS. 16 and 17 is shown with respect to drilling bone, the method can be to drill other materials.

As shown in FIG. 16, the drill guide 18 is advanced through a skin 300 of a patient toward a target 302 to be drilled, which is bone. The distal end of the drill guide 18 is positioned at a desired angle relative to a surface 304 of the bone, which as shown in FIG. 16 is perpendicular thereto. The drill guide 18 is advanced directly through the skin 300 but can be advanced through an introducer device, such as a cannula, positioned in the skin 300. The drill assembly 10 is advanced into the patient's body through the cannulated interior of the drill guide 18 and is advanced through the drill guide 18 to advance the drill tip 12 distally beyond the drill guide's distal end. The drill assembly 10 is then drilled into the bone 302, as shown in FIG. 17, to form a hole in the bone 302 in which, for example, an implant and/or a graft can be positioned.

A person skilled in the art will appreciate that the implementations described herein have application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the drill assembly and methods based on the above-described embodiments. Accordingly, this disclosure is not to be limited by what has been particularly shown and described, except as indicated by the appended claims. All publications and references cited herein are expressly incorporated herein by reference in their entirety.

What is claimed is:

1. A drill assembly comprising:
   a shaft having a longitudinal axis and a distal end;
   a drill tip disposed distally of the distal end of the shaft;
   a flexible element disposed between the drill tip and the shaft, wherein the flexible element includes a plurality of wires twisted together, and the flexible element is configured to move from a substantially linear configuration aligned with the longitudinal axis to a curved configuration with respect to the longitudinal axis; and
   a monolithic conformal covering disposed on the flexible element, having a thickness that varies along a length of the flexible element and that defines a flute extending helically around the flexible element, and configured to reduce diametric expansion of the flexible element due to compressive forces when the flexible element is in the curved configuration and is capable of transmitting bidirectional torque.

2. The drill assembly of claim 1, wherein the flexible element and the covering are configured such that torque is transmitted through the shaft to the drill tip via the flexible element and the covering when the flexible element is in the curved configuration.

3. The drill assembly of claim 1, wherein the flute is oriented to remove material during drilling.

4. The drill assembly of claim 1, wherein the conformal covering comprises a polymeric material.

5. The drill assembly of claim 1, wherein the conformal covering encapsulates the flexible element.

6. The drill assembly of claim 1, further comprising a drill guide, wherein the flexible element having the conformal covering disposed thereon is at least partially disposed within the drill guide, the flexible element having the conformal covering disposed thereon being rotatable and translatable within the drill guide.

7. The drill assembly of claim 6, wherein the drill guide comprises an elongate proximal body having a longitudinal axis and a distal portion that is angled with respect to the longitudinal axis.

8. A drill assembly comprising:
   a rigid shaft having a first longitudinal axis and a distal end;
   a pointed drill tip disposed distally of the distal end of the shaft;
   a flexible element disposed between the drill tip and the shaft and having a second longitudinal axis, the flexible element including a plurality of wires twist together in a first helical direction, the flexible element being configured to transmit torque when the flexible element is rotated in the first helical direction; and
   a monolithic conformal covering disposed on the flexible element, having an outer surface defining a helical flute extending around the flexible element and configured to reduce diametric expansion of the flexible element when the flexible element is rotated in a second helical direction that is opposite the first helical direction.

9. The drill assembly of claim 1, wherein a distal end of the flexible element is disposed in a first hole formed in a proximal end of the drill tip, and a proximal end of the flexible element is disposed in a second hole formed in the distal end of the shaft.

10. The drill assembly of claim 1, wherein the shaft is rigid.

11. The drill assembly of claim 8, wherein the flexible element is configured to be advanced through a drill guide and to automatically flex from a substantially linear configuration to a curved configuration when advanced through a distal portion of the drill guide.

12. The drill assembly of claim 11, wherein the first longitudinal axis of the shaft and a third longitudinal axis defined by a proximal portion of the drill guide are aligned when the flexible element is in the substantially linear configuration and when the flexible element is in the curved configuration, and the first longitudinal axis of the shaft and a fourth longitudinal axis defined by the distal portion of the drill guide are aligned when the flexible element is in the substantially linear configuration and are not aligned when the flexible element is in the curved configuration.

13. The drill assembly of claim 8, wherein the at least one helical flute is oriented to remove material during drilling.

14. The drill assembly of claim 8, wherein the at least one helical flute is oriented in the second helical direction.

15. The drill assembly of claim 8, wherein the conformal covering comprises a polymeric material.

16. The drill assembly of claim 8, wherein a distal end of the flexible element is disposed in a first hole formed in a proximal end of the drill tip, and a proximal end of the flexible element is disposed in a second hole formed in the distal end of the shaft.

* * * * *